(12) United States Patent
Glossop

(10) Patent No.: US 7,840,254 B2
(45) Date of Patent: Nov. 23, 2010

(54) ELECTROMAGNETICALLY TRACKED K-WIRE DEVICE

(75) Inventor: Neil David Glossop, Toronto (CA)

(73) Assignee: Philips Electronics Ltd, Vancouver, British Columbia (CA)

( * ) Notice: Subject to any disclaimer, the term of this patent is extended or adjusted under 35 U.S.C. 154(b) by 1212 days.

(21) Appl. No.: 11/333,364

(22) Filed: Jan. 18, 2006

(65) Prior Publication Data

US 2006/0173291 A1 Aug. 3, 2006

Related U.S. Application Data

(60) Provisional application No. 60/644,007, filed on Jan. 18, 2005.

(51) Int. Cl.
*A61B 5/05* (2006.01)

(52) U.S. Cl. ...................................... 600/424

(58) Field of Classification Search ............ 606/1, 606/2, 10, 13, 14, 300–321; 600/407, 595, 600/42

See application file for complete search history.

(56) References Cited

U.S. PATENT DOCUMENTS

| | | | |
|---|---|---|---|
| 3,021,842 A | 2/1962 | Flood | |
| 4,080,706 A | 3/1978 | Heilman et al. | 29/173 |
| 4,279,252 A | 7/1981 | Martin | 128/349 R |
| 4,600,017 A | 7/1986 | Schroeppel | |
| 4,697,595 A | 10/1987 | Breyer et al. | 128/660 |
| 4,722,056 A | 1/1988 | Roberts et al. | 364/413 |
| 4,777,951 A | 10/1988 | Cribier et al. | 128/344 |
| 4,887,606 A | 12/1989 | Yock et al. | 128/662.05 |
| 4,895,168 A | 1/1990 | Machek | 128/772 |
| 4,935,019 A | 6/1990 | Papp, Jr. | 604/362 |
| 4,961,433 A | 10/1990 | Christian | 128/772 |
| 5,042,486 A | 8/1991 | Pfeiler et al. | 128/653 R |
| 5,045,080 A | 9/1991 | Dyer et al. | 604/362 |
| 5,116,345 A | 5/1992 | Jewell et al. | 606/130 |
| 5,187,658 A | 2/1993 | Cline et al. | 364/413.13 |
| 5,204,625 A | 4/1993 | Cline et al. | 324/306 |
| 5,207,675 A | 5/1993 | Canady | 606/40 |
| 5,211,165 A | 5/1993 | Dumoulin et al. | 128/653.1 |
| 5,221,283 A | 6/1993 | Chang | 606/130 |
| 5,242,441 A | 9/1993 | Avitall | |
| 5,247,935 A | 9/1993 | Cline et al. | 128/653.2 |
| 5,251,127 A | 10/1993 | Raab | 364/413.13 |
| 5,251,635 A | 10/1993 | Dumoulin et al. | 128/653.2 |
| 5,255,680 A | 10/1993 | Darrow et al. | 128/653.1 |

(Continued)

FOREIGN PATENT DOCUMENTS

AU 6367896 2/1997

(Continued)

OTHER PUBLICATIONS

Knaan, Dotan, et al., Effective Intensity-Based 2D/3D Rigid Registration Between Fluoroscopic X-Ray and CT, *MICCAI*, vol. 1, 2003, pp. 351-358.

(Continued)

*Primary Examiner*—Brian Casler
*Assistant Examiner*—Elmer Chao

(57) ABSTRACT

Devices and methods for registering, dynamically referencing, and navigating an anatomical region of interest of a patient are provided using a tracked Kirschner wire (K-wire), where the K-wire includes a position-indicating element.

21 Claims, 10 Drawing Sheets

U.S. PATENT DOCUMENTS

| | | | |
|---|---|---|---|
| 5,265,610 A | 11/1993 | Darrow et al. | 128/653.1 |
| 5,271,400 A | 12/1993 | Dumoulin et al. | 128/653.2 |
| 5,275,165 A | 1/1994 | Ettinger et al. | 128/653.2 |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | 128/653.2 |
| 5,304,933 A | 4/1994 | Vavrek et al. | 324/318 |
| 5,305,203 A | 4/1994 | Raab | 364/413.13 |
| 5,307,812 A | 5/1994 | Hardy et al. | 128/653.2 |
| 5,318,025 A | 6/1994 | Dumoulin et al. | 128/653.2 |
| 5,323,779 A | 6/1994 | Hardy et al. | 128/653.2 |
| 5,327,884 A | 7/1994 | Hardy et al. | 128/653.2 |
| 5,353,808 A | 10/1994 | Viera | 128/772 |
| 5,365,927 A | 11/1994 | Roemer et al. | 128/653.2 |
| 5,368,031 A | 11/1994 | Cline et al. | 128/653.2 |
| 5,368,032 A | 11/1994 | Cline et al. | 128/653.2 |
| 5,377,678 A | 1/1995 | Dumoulin et al. | 128/653.1 |
| 5,383,454 A | 1/1995 | Bucholz | 128/653.1 |
| 5,383,465 A | 1/1995 | Lesny et al. | 128/662.05 |
| 5,386,828 A | 2/1995 | Owens et al. | 128/653.1 |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | 128/849 |
| 5,400,383 A | 3/1995 | Yassa et al. | 378/98.2 |
| 5,437,277 A | 8/1995 | Dumoulin et al. | 128/653.1 |
| 5,443,066 A | 8/1995 | Dumoulin et al. | 128/653.1 |
| 5,443,068 A | 8/1995 | Cline et al. | 128/653.5 |
| 5,445,150 A | 8/1995 | Dumoulin et al. | 128/653.1 |
| 5,465,732 A | 11/1995 | Abele | 128/772 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | 128/653.1 |
| 5,526,814 A | 6/1996 | Cline et al. | 128/653.2 |
| 5,558,091 A | 9/1996 | Acker et al. | 128/653.1 |
| 5,603,318 A | 2/1997 | Heilbrun et al. | 128/630 |
| 5,645,065 A | 7/1997 | Shapiro et al. | 128/653.1 |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | 364/474.24 |
| 5,715,822 A | 2/1998 | Watkins et al. | 128/653.5 |
| 5,740,802 A | 4/1998 | Nafis et al. | 128/653.1 |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,873,845 A | 2/1999 | Cline et al. | 601/3 |
| 5,880,976 A | 3/1999 | DiGioia, III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 6,016,439 A | 1/2000 | Acker | 600/411 |
| 6,036,682 A | 3/2000 | Lange et al. | 604/529 |
| 6,073,043 A | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,188,355 B1 | 2/2001 | Gilboa | 342/448 |
| 6,192,279 B1 | 2/2001 | Barreras, Sr. | |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |
| 6,210,339 B1 | 4/2001 | Kiepen et al. | 600/486 |
| 6,216,029 B1 | 4/2001 | Paltieli | 600/427 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 | 10/2001 | von der Ruhr et al. | 600/338 |
| 6,314,310 B1 | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,343,496 B1 * | 2/2002 | Hanna et al. | 72/61 |
| 6,356,783 B1 | 3/2002 | Hubbard, Jr. | 600/546 |
| 6,380,732 B1 | 4/2002 | Gilboa | 324/207.17 |
| 6,381,485 B1 | 4/2002 | Hunter et al. | 600/407 |
| 6,383,174 B1 | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/407 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 607/117 |
| 6,529,758 B2 | 3/2003 | Shahidi | 600/407 |
| 6,547,782 B1 * | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,127 B1 | 7/2003 | McKinnon | 600/411 |
| 6,591,129 B1 | 7/2003 | Ben-Haim et al. | 600/424 |
| 6,593,884 B1 | 7/2003 | Gilboa et al. | 342/448 |
| 6,615,155 B2 | 9/2003 | Gilboa | 702/150 |
| 6,615,695 B1 * | 9/2003 | Hjelle et al. | 82/1.11 |
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,386,339 B2 | 6/2008 | Strommer et al. | 600/424 |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0143317 A1 | 10/2002 | Glossop | 604/529 |

| | | | |
|---|---|---|---|
| 2002/0156363 A1 | 10/2002 | Hunter et al. | 600/410 |
| 2002/0156417 A1 | 10/2002 | Rich et al. | 604/65 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0050644 A1* | 3/2003 | Boucher et al. | 606/90 |
| 2003/0074011 A1 | 4/2003 | Gilboa et al. | 606/130 |
| 2003/0092988 A1 | 5/2003 | Makin | 600/439 |
| 2003/0109934 A1* | 6/2003 | Lewandrowski et al. | 623/23.59 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0135388 A1* | 7/2003 | Martucci et al. | 705/2 |
| 2003/0171680 A1 | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/424 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1 | 11/2004 | Miller | 128/207.14 |
| 2004/0234933 A1 | 11/2004 | Dawson et al. | 434/262 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0182319 A1 | 8/2005 | Glossop | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| AU | 722539 | 8/2000 |
| BR | 9609484 | 12/1999 |
| CA | 2226938 | 2/1997 |
| DE | 69420228 D | 9/1999 |
| DE | 69420228 T | 4/2000 |
| EP | 0 845 959 | 6/1998 |
| EP | 0 654 244 | 8/1999 |
| IL | 0107523 | 1/2000 |
| IL | 0114610 | 7/2000 |
| JP | 2000500031 T | 1/2000 |
| WO | WO 97/03609 | 2/1997 |
| WO | WO 98/56295 | 12/1998 |
| WO | WO 00/22904 | 4/2000 |

OTHER PUBLICATIONS

Gee, A. H., et al., "3D Ultrasound Probe Calibration Without a Position Sensor", CUED/F-INFENG/TR 488, University of Cambridge, Department of Engineering, Sep. 2004, 21 pages.

Lindseth, Frank, et al., "Probe Calibration for Freehand 3D Ultrasound Reconstruction and Surgical Navigation", Dec. 2002, 27 pages.

Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

RITA StarBurst Soft Tissue Access System and RITA StarBurst Hard Tissue Access System, http://www.ritamedical.com, Rita Medical Systems, Inc., copyright 2002, , 8 pages.

Cool-tip RF Tissue Ablation System, Cool-tip RF System, and Cool-tip Electrodes, http://www.valleylab.com/static/cooltip/products.html, Valleylab, copyright 2004, 4 pages.

LeVeen Needle Electrode, Boston Scientific, printed from http://www.bostonscientific.com/med_specialty/deviceDetail.jhtml?task=_tskBasicDevice..., printed on Sep. 13, 2004, 1 page.

Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

Tanase, Dafina, et al., "Magnetic Sensors for Use on Guide Wires or Catheters", in SeSens 2001, in press 2002, pp. 868-872.

Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

Solomon, Stephen B., et al., "Real-Time Cardiac Catheter Navigation on Three-Dimensional CT Images", *Journal of Interventional Cardiac Electrophysiology*, vol. 8, 2003, pp. 27-36.

Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

Baert, Shirley A. M., et al., "Endpoint Localization in Guide Wire Tracking During Endovascular Interventions", *Academic Radiology*, vol. 10, No. 12, Dec. 2003, pp. 1424-1432.

Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

Baert, Shirley A. M., et al., "Guide-Wire Tracking During Endovascular Interventions", *IEEE Transactions on Medical Imaging*, vol. 22, No. 8, Aug. 2003, pp. 965-972.

Kobashi, Keiji, et al., "A New Biomechanical Model Based Approach on Brain Shift Compensation", *MICCAI 2003*, LNCS 2878, 2003, pp. 59-66.

Timinger, Holger, et al., "Motion Compensation for Interventional Navigation on 3D Static Roadmaps Based on an Affine Model and Gating", *Physics in Medicine and Biology*, vol. 49, 2004, pp. 719-732.

Lorigo, Liana M., et al., "Curves: Curve Evolution for Vessel Segmentation", *Medical Image Analysis*, vol. 5, 2001, pp. 195-206 (pp. 1-14).

Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.

Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.

"Semi-Automatic Registration for Image Guided Surgery", Traxtal poster presented at CAOS '99 (Computer Assisted Orthopaedic Surgery, 4$^{th}$ International Symposium), MICCAI, Mar. 17-19, 1999, Davos, Switzerland, 1 page.

Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.

Livyatan, Harel, "Calibration and Gradient-Based Rigid Registration of Fluoroscopic X-raysto CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.

SuperDimension, Ltd, web page, updated in Sep. 2005, 1 page.

Schweikard, Achim, et al., "Robotic Motion Compensation for Respiratory Movement During Radiosurgery", *Computer Aided Surgery*, vol. 5, 2000, pp. 263-277.

Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.

Ellsmere, James, et al., "A Navigation System for Augmenting Laparoscopic Ultrasound", Center for Integration of Medicine and Innovative Technology, Cambridge, Massachusetts, 8 pages.

Hofstetter, R., et al., "Fluoroscopy Based Surgical Navigation—Concept and Clinical Applications", Maurice E. Muller Institute for Biomechanics, University of Bern, Switzerland, 1997, 3 pages.

Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

Summers, Ronald M., et al., "Colonic Polyps: Complementary Role of Computer-Aided Detection in CT Colonography", *Radiology*, vol. 225, No. 2, Nov. 2002, pp. 391-399.

Hara, A. K., et al., "Reducing Data Size and Radiation Dose for CT Colonography", *AJR*, vol. 168, May 1997, pp. 1181-1184.

\* cited by examiner

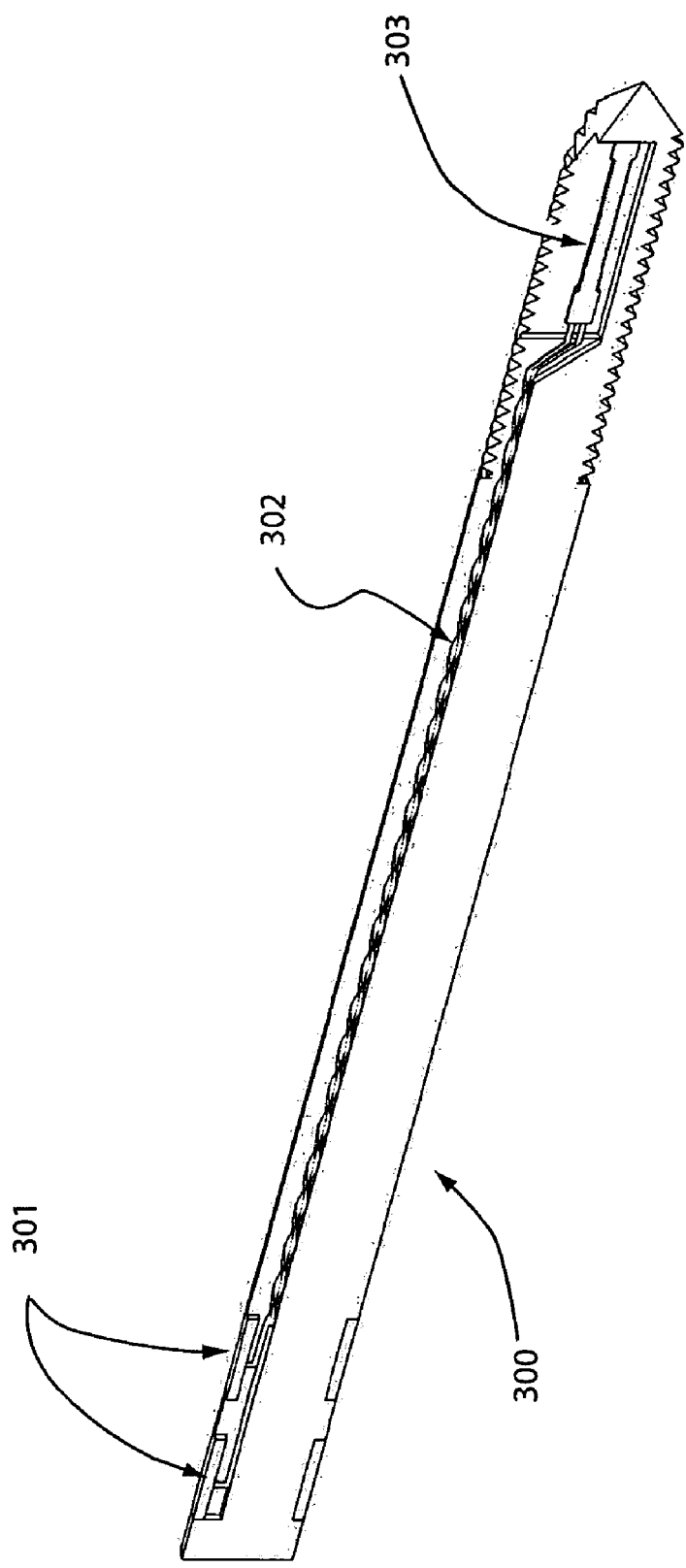
Fig 3

ELECTROMAGNETICALLY TRACKED K-WIRE DEVICE

RELATED APPLICATIONS

This application claims priority to U.S. Provisional Patent Application Ser. No. 60/644,007, filed Jan. 18, 2005, which is hereby incorporated by reference herein in its entirety.

FIELD OF THE INVENTION

The invention relates to electromagnetically tracked K-wire devices.

BACKGROUND OF THE INVENTION

Image-guided surgery systems use a position sensor system to graphically overlay an iconic representation of a tracked surgical instrument onto pre-acquired images (e.g., CT, MR, fluoroscopic X-ray or other images) of the patient. Current state of the art tracking employs optical systems characterized by a high degree of accuracy. However, the ergonomics of these systems are poor, and optical systems require that tracked objects remain in the camera's line of sight, relatively distant from the instrument tip. The relatively heavy and large position-indicating elements must be attached to rigid instruments to achieve the required accuracy. In particular, maintaining a line of sight path can be cumbersome for the physician and complicate the already delicate operating environment. Together, these drawbacks may lower the acceptance of computer-assisted surgery among physicians.

A new generation of electromagnetic trackers, with increased accuracy and the ability to track objects in ferromagnetic environments, is becoming available. Electromagnetic tracking systems do not require that a direct line of sight be maintained. In addition, these new generation electromagnetic trackers ("position sensors") use position-indicating elements that are extremely small. The systems normally consist of a control unit, sensor interface device, and field generator. The position-indicating elements consist of small coils that connect to the sensor interface unit.

Image guidance workstations for use in spine surgery have been commercially available for over a decade. These existing CAS workstations are based on optical tracking systems, which do not allow accurate tracking of flexible instrumentation. Flexible instrumentation is generally smaller and less invasive than rigid instrumentation. Current minimally invasive CAS techniques have been limited to rigid instruments due to the tracking technology.

K-wires in general are known. In present clinical practice, K-wires are an essential part of many orthopaedic procedures including spinal fusion, fracture fixation and stabilization. K-wires can also serve as a guides or "trials" for screw placement during instrumented fixation. In some surgical procedures, the K-wires are used to stabilize or manipulate the bones. In others, cannulated screws may be inserted over the K-wire and placed through the bone either to serve as anchor points for plates or stabilizing hardware, or to unite a fracture. The K-wire may be removed or left in place at the end of the procedure. Other uses are possible.

Any misplacement of the K-wire can result in misplacement of the screw or misalignment of a fracture, with potentially catastrophic consequences for the patient. For example, if the K-wire is placed through a critical structure such as a nerve or blood vessel during a spine operation, paralysis or death could result. Misplaced wires can result in decrease in integrity of the fusion or reduced strength of any construct. K-wires are often inserted percutaneously into the bone making it difficult to know where the wire is going without constant x-rays.

One of the drawbacks of conventional image-guided surgery is that the instrument that is actually tracked is usually the holder or driver of the inserted tool. For example, K-wires are often tracked by tracking the drill or a drill guide used to install them, which is proximal to the end actually inserted in the patient. While the tip of a stiff or rigid instrument may remain static with respect to the tracker, a thin proximally tracked K-wire might easily bend during drilling or placement, rendering a trajectory-based on the proximally placed tracker prone to error. This deviation may be easily overlooked as it may occur unless constant imaging is used or the position of the wire is directly and continually viewed by the physician. This later option is essentially impractical in minimally invasive surgery however.

Also, given the static nature of the backdrop projection images in image guided surgery, this error would not be detected during a conventional image guided surgical procedure until a fluoroscopic view is taken.

Other problems and drawbacks exist with known systems and techniques.

SUMMARY OF THE INVENTION

An object of the invention is to overcome at least some of these and/or other drawbacks of prior systems and techniques.

One aspect of the invention relates to a method for directly tracking the tip of the K-wire (e.g., electromagnetically). Among other things this may provide a significant improvement and can lead to increased accuracy and decreased use of intra-operative X-rays. In contrast, optical tracking systems generally are not capable of effectively tracking the tip since they are typically limited to line of sight applications. This makes it difficult for them to track the distal end of the K-wire that is implanted in the patient. The electro-magnetically tracked K-wires would offer a dramatic reduction in surgical invasiveness as compared with current CAS procedures. They would be compatible with existing CAS modalities including conventional (point match registration), virtual fluoroscopy and 2D-3D. In addition to aiding in cannulating the pedicle, a tracked K-wire could potentially assist in other aspects of the current technique including registration, dynamic referencing and verification of registration.

According to one embodiment, the invention comprises a K-wire having a shaft section, a tip section and an optionally threaded portion along all or part of its length. The K-wire contains an electromagnetically tracked position-indicating element near its tip. Lead-wires of the position-indicating element may be connected to conductive connection bands. The connection bands may be placed at the proximal end of the K-wire. To facilitate placement of the position-indicating element and wiring, a groove may be machined along the length of the K-wire. The position-indicating element can be embedded into a groove machined into the tip of the K-wire.

The various objects, features, and advantages of the invention will be apparent through the detailed description of the preferred embodiments and the drawings attached hereto. It is also to be understood that the following detailed description is exemplary and not restrictive of the scope of the invention.

BRIEF DESCRIPTION OF THE DRAWINGS

FIG. 3 depicts a cross section showing the tracked K-wire according to one embodiment of the invention.

DETAILED DESCRIPTION

Figure 1:
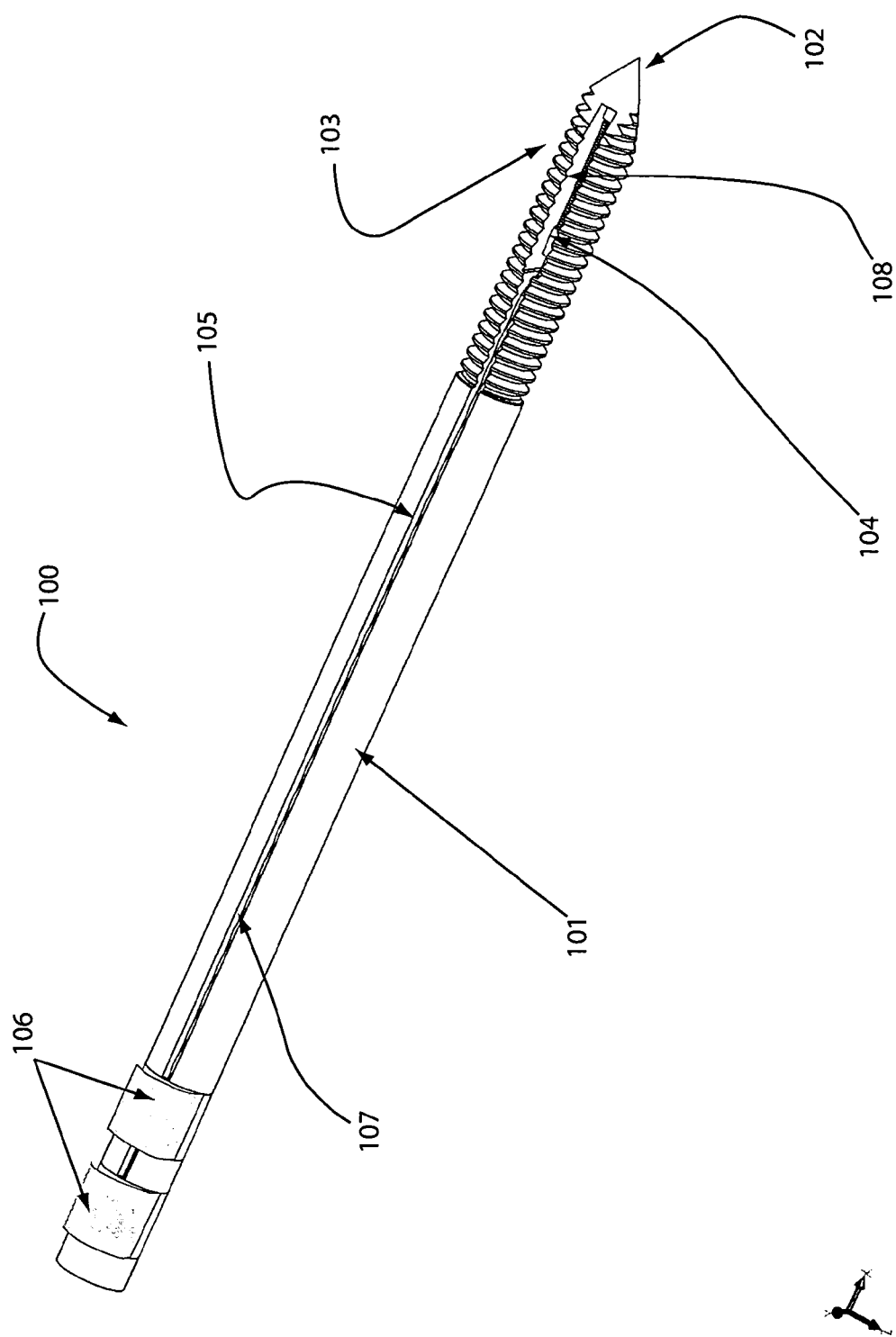
FIG. 1 depicts a schematic illustration of the K-wire according to one embodiment of the invention.

One embodiment of the invention is shown by way of example in FIG. 1. As shown, the device includes a K-wire 100 comprised of a shaft section 101, a tip section 102, and an optionally threaded portion 103, along all or part of its length. The K-wire contains at least one electromagnetically tracked position-indicating element 104 embedded near its tip. The lead-wires 105 of the position-indicating element are connected to connection bands 106, which may be coated with gold or other suitable conductive coating. The connection bands may be placed at the proximal end of the K-wire or otherwise.

To facilitate placement of the position-indicating element and wiring, a groove 107 may be machined along all or part of the length of the K-wire. The tip 102 is preferentially made sharp, for example as a trocar 3 point tip. Likewise, the position-indicating element 104 can be embedded into a groove 108, machined into the tip of the K-wire.

Figure 2:
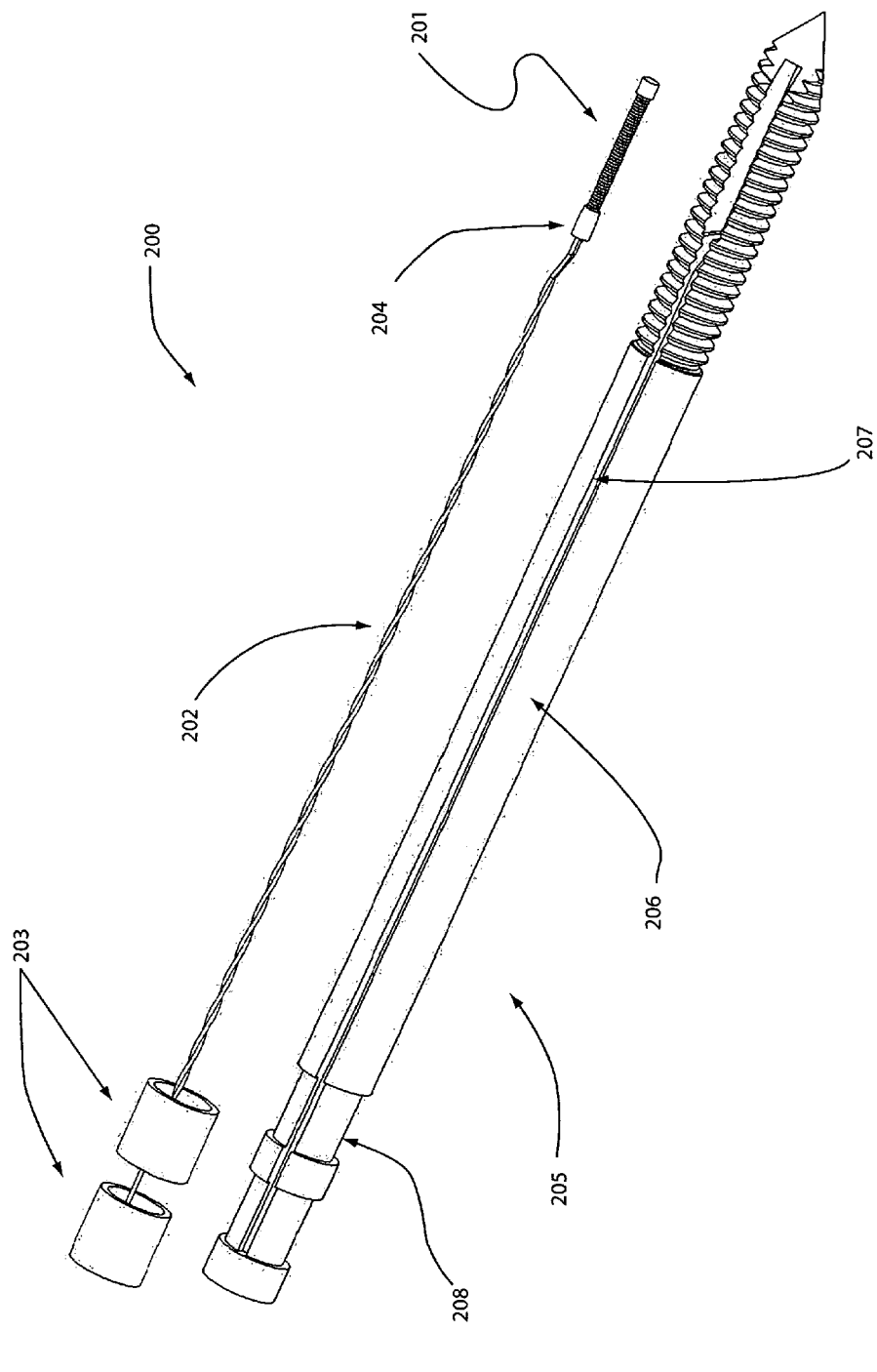
FIG. 2 depicts an exploded view of the K-wire according to one embodiment of the invention.

FIG. 2 depicts an exploded view of the K-wire 200 according to one embodiment of the invention. FIG. 2 depicts various components. Numeral 201 denotes the electrical components of the device including the position-indicating element, the leadwires 202, and the connection bands 203. As shown, radio-opaque fiducials are included on or around the position-indicating element coil 204 to assist in radiologically locating the position-indicating element as an adjunct to registration, dynamic referencing or verification of system accuracy.

These fiducials are described in detail in U.S. Pat. No. 6,785,571, to Glossop, which is hereby incorporated by reference herein in its entirety. However the invention is not so limited. These fiducials may or may not be present in the various configurations of the device and other techniques may be used. Various mechanical parts of the system are indicated as 205, which includes the shaft 206, the milled groove features 207, for burying the position-indicating element and wires beneath the main shaft body so they do not become damaged when the K-wire is drilled into bone. Features 208 are used to assist with assembly of the electrical contacts, 203 and may incorporate insulation layers (not shown). Other components may also be used.

FIG. 3 shows a cross section showing the tracked K-wire 300. The connection bands are shown at 301. The connection wires 302 are inside the groove and the position-indicating element 303 is embedded in the groove. Position-indicating element 303 may be placed along the longitudinal axis of rotation of the K-wire or otherwise.

Figures 4A, 4B:
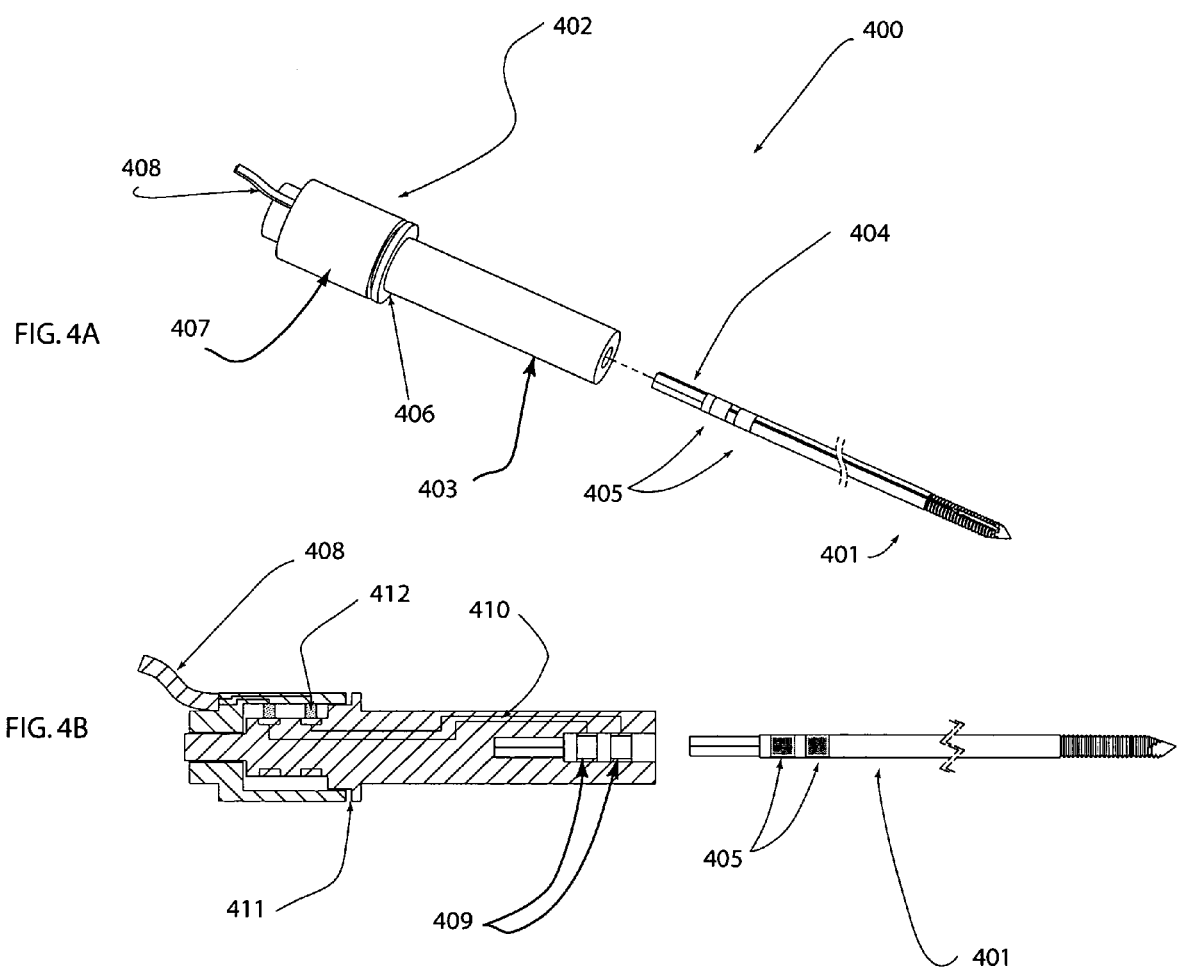
FIG. 4A depicts a tracked K-wire and a slip coupling mechanism according to an embodiment of the invention.
FIG. 4B depicts a tracked K-wire and a cross section of a slip coupling mechanism according to an embodiment of the invention.

FIGS. 4A and 4B depict additional items that may be used in a K-wire connection assembly 400 according to one embodiment of the invention. In order to maintain contact of the position-indicating element while drilling the K-wire into place, the connection bands can be connected to a slip ring or slip coupling. Slip rings and slip couplings generally are known. Element 401 represents the tracked K-wire and element 402 refers to a slip-coupling mechanism. Slip couplings are available commercially to a high degree of accuracy and reliability.

The connection bands may be made from any conductive material. In one embodiment they can be fabricated from stainless steel. In some embodiments, the bands can be made from a material plated with a conductive material such as gold. Other connection bands can be used. Other types of connectors may also be used, including, for example, spot connectors, axial connectors, or other type of connection enabling electrical signals from the position-indicating element to be connected to an external device.

Two examples of coupling mechanisms are shown. Others can be used. In the embodiment depicted in FIGS. 4A and 4B, a commercial coupling is specifically modified with an adaptor socket portion 403 capable of accepting the shaft of the K-wire. The K-wire depicted here has a hexagonal or other non-rotational head 404 machined on it. The K-wire's contacts 405, non-rotationally couple to the adaptor socket 403. The adaptor socket may be fixed permanently to the rotational portion of the coupling 406 so that the signals from the position-indicating element are conducted through the fixed portion of the coupling 407 and out through the leads 408.

The cross sectional view (FIG. 4B) shows additional details of the device, according to one embodiment of the invention. Contacts 409 may be fixed contacts inside the receptacle. These contacts mate with the K-wire and remain relatively stationary with respect to it. The wires 410 may be wires intrinsic to the slip coupling. These wires 410 may lead back through the slip coupling 411 and the high quality rotation contacts 412. This design makes use of reusable, high quality commercial components mated with a lower tolerance disposable component in which the connection need not be as high quality. However, the invention is not so limited.

In another embodiment, not shown, a commercial coupling is not employed. Instead a custom coupling is constructed. The custom coupling may use brushes similar to those used in commercial rotational couplings or electrical motors. The brushes directly contact the annular bands. Other couplings and coupling techniques may be used.

Figure 5:
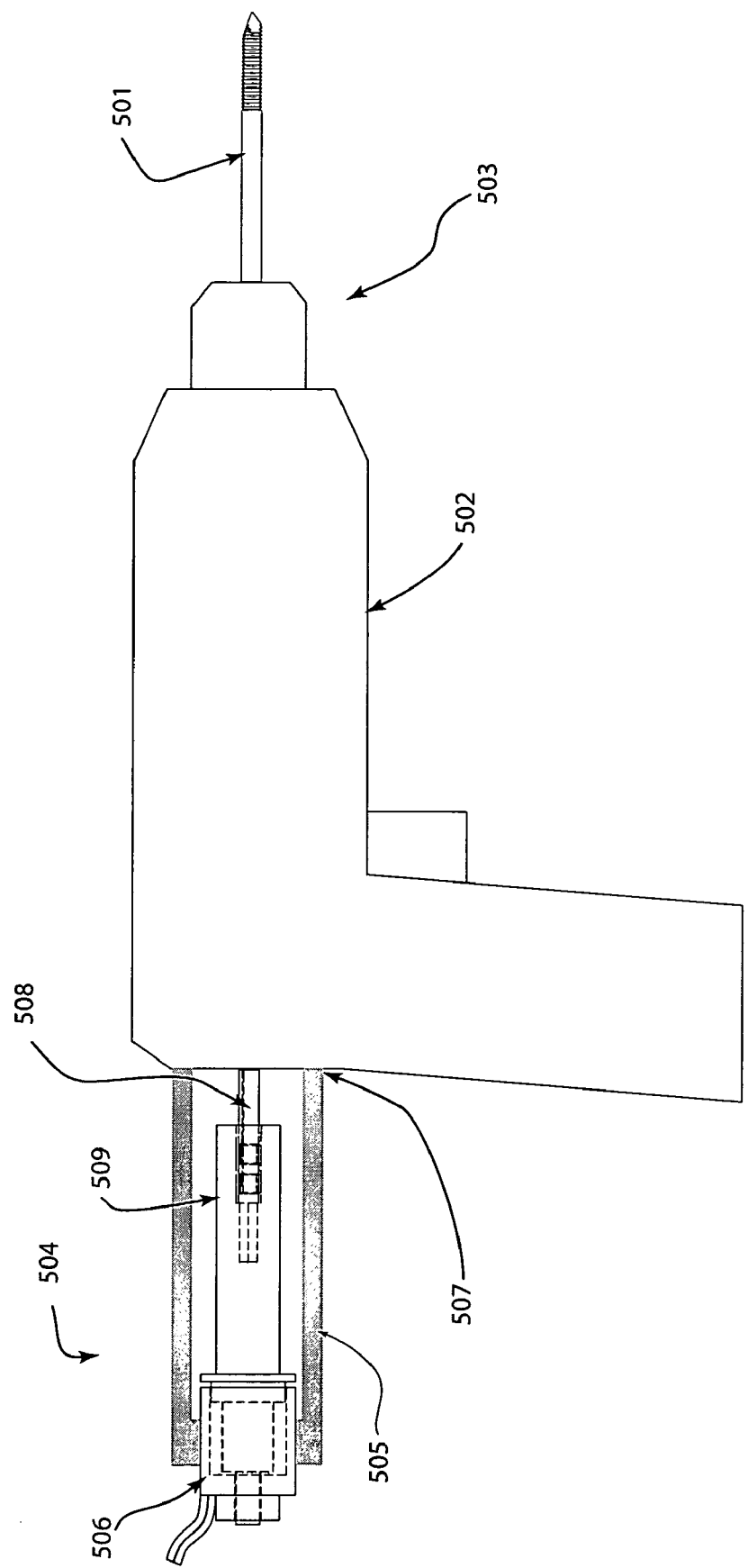
FIG. 5 depicts a tracked K-wire attached to a power drill, according to one embodiment of the invention.

FIG. 5 shows an instrumented K-wire 501 attached to a power drill 502. A similar setup can be employed for a manual drill or other tools. As shown, a K-wire 501 is inserted into chuck 503 of a cannulated drill. The drill 502 may be equipped with a coupling assembly 504 (e.g., the slip coupling assembly described in FIG. 4 above). The proximal portion of the slip coupling is attached to the drill so that it does not rotate with respect to the drill. The method of connection shown here, 505, is a brace or sleeve that fixes the proximal end of the slip coupling 506 to the drill at location say 507. Other couplings may be used. The length of the coupling (e.g., brace or sleeve 505) can be adjustable, if desired. The brace or sleeve prevents the proximal end of the slip-coupling from rotating. The guidewire, the proximal end of which is marked as 508 is inserted into the distal end of the slip coupling 509, which is locked to move (e.g. through the use of the hex head) with the guidewire. Thus, as the K-wire is drilled, electrical connections can continually sample the location and orientation of the position-indicating element in the K-wire during the drilling process without wires becoming twisted. When the K-wire is in position, it can be temporarily or permanently decoupled from the drill and slip coupling. It may also be cut or otherwise controlled in the usual manners that such devices are used.

Figure 6:
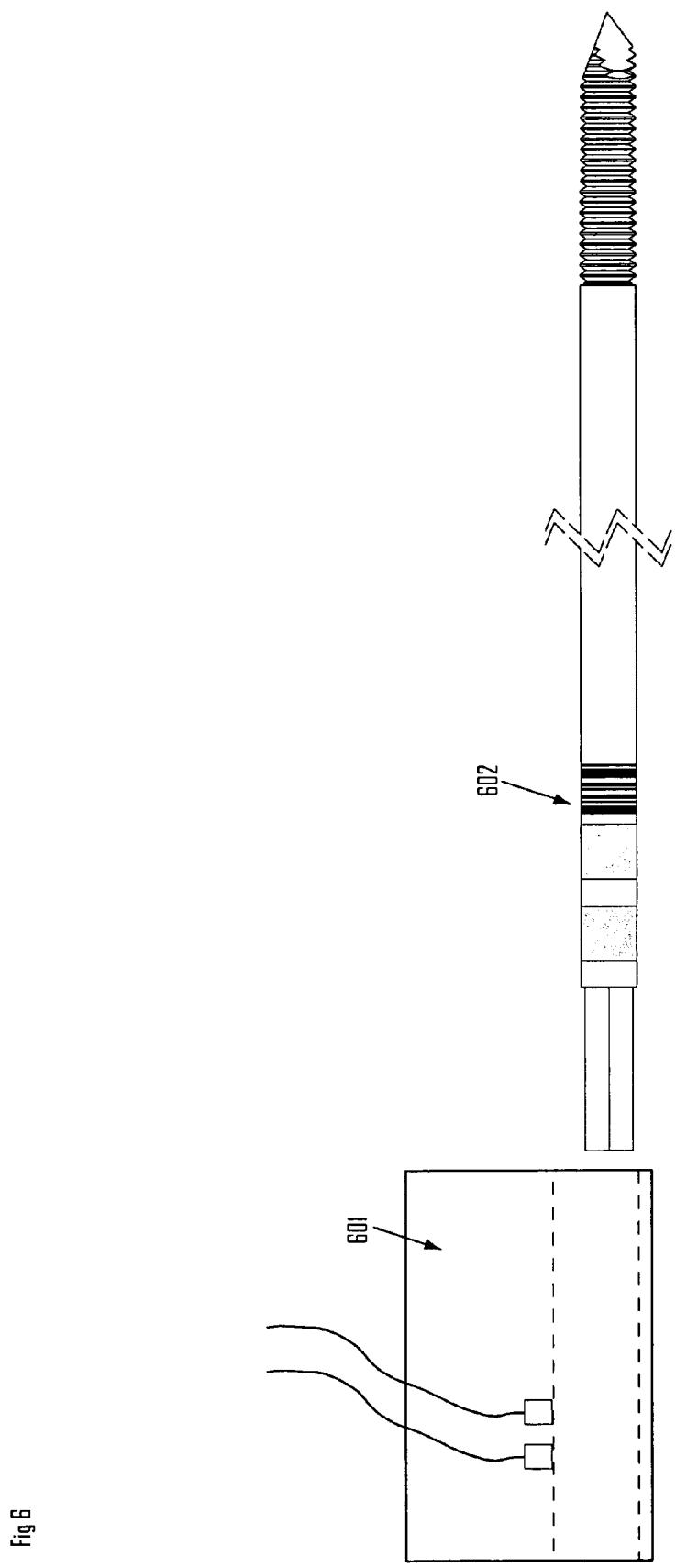
FIG. 6 depicts a non-rotary coupling used to achieve contact with the position-indicating elements embedded in the K-wire, according to one embodiment of the invention.

In another embodiment shown in FIG. 6, a non-rotary coupling 601 may be used to achieve contact with the position-indicating elements embedded in the K-wire. This coupling slips over the head of the K-wire and achieves contact by providing a mechanism that engages the connection bands on the tracked K-wire. Alternatively, this coupling mechanism may be used if the K-wire is already in position (as it would be if the K-wire is being used as a dynamic reference or registration device). Or the coupling mechanism may be used instead of the slip coupling, for example, if the K-wire does not need to be rotated excessively, such as might be used with an intra-meduallary nail or similar device. Both the slip coupling and the non-rotary coupling may be used interchangeably.

In an embodiment illustrated in FIG. 6, numeral 602, a bar code, RFID chip, switch array or other indicator may be added to the K-wire. This indicator may incorporate information specific to the tool such as the serial number, date of manufacture, information specific to the position-indicating element, device-position-indicating element combination such as the position-indicating element to tip offset and/or other tool information. Various other information may also be included.

In one embodiment, the diameter of the contact region may be the same as or smaller that the diameter of the K-wire. This permits existing devices such as cannulated screws or other instruments to be passed over the tracked K-wire in the same manner that it currently is done using conventional K-wires.

Figure 7:
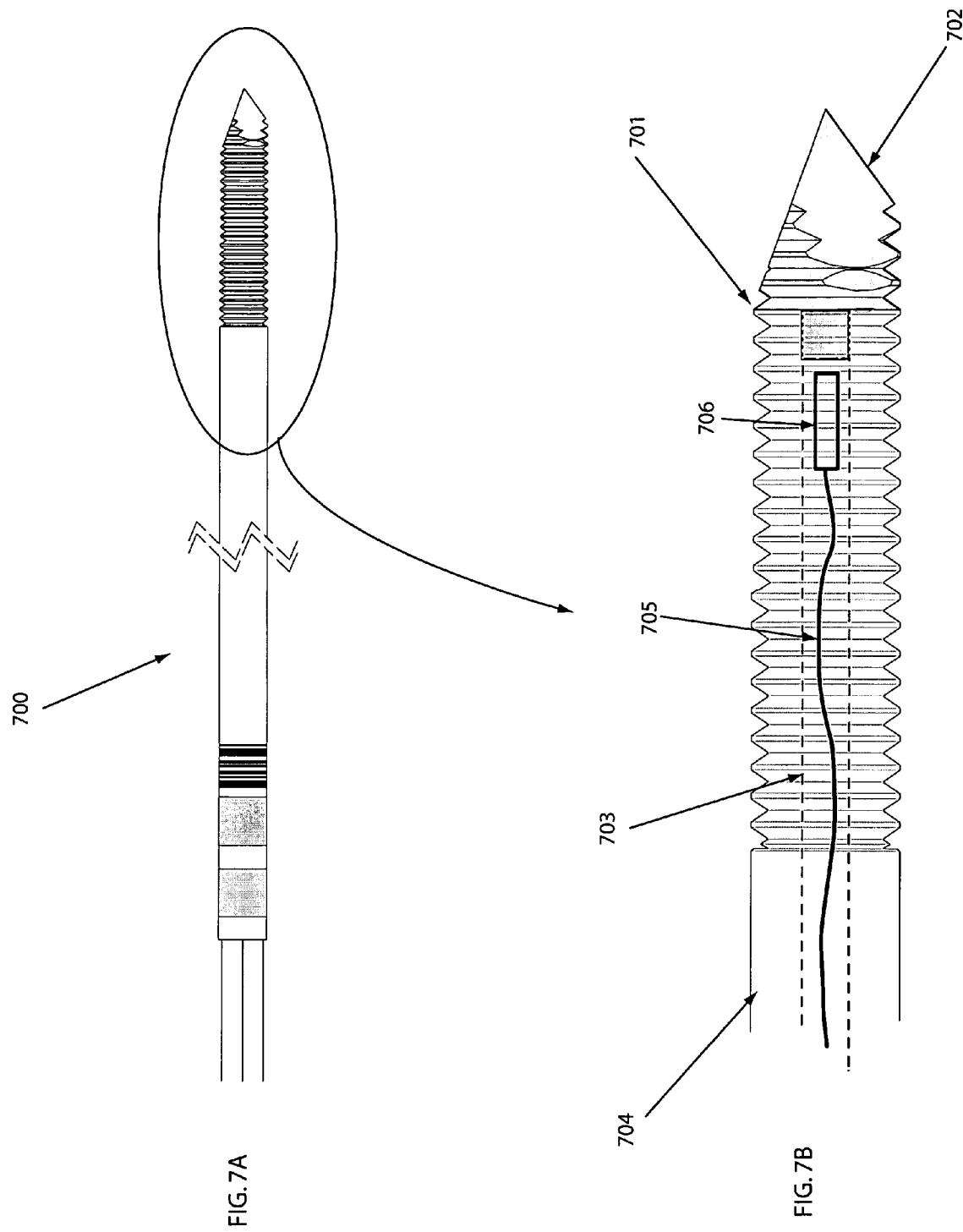
FIG. 7A depicts a tracked K-wire according to an embodiment of the invention.
FIG. 7B depicts the tip of a tracked K-wire according to an embodiment of the invention.

In an alternate embodiment, shown in FIGS. 7A and 7B, the tracked K-wire 700 is constructed by drilling a hole along the shaft of a K-wire or fabricating one from a thick walled tube 704. The position-indicating element 706 and associated wiring 705 may be placed in the interior lumen of the tube 703, and connection bands added to the proximal end. A closed, sharp tip 702 may be welded onto hollow tube 704 at point 701 using, for example, a laser weld process. A drawing process may also be used to form the tip into a closed, pointed form.

The tracked K-wire may be used as a guided instrument, as a device to facilitate registration, as a dynamic reference device, as a verification device or otherwise. Examples of methods of registration, dynamic referencing, verification and other methods can be found in U.S. patent application Ser. No. 11/059,336 (published as U.S. Patent Publication No. 20050182319) by Glossop, which is hereby incorporated by reference herein in its entirety.

Figure 8:
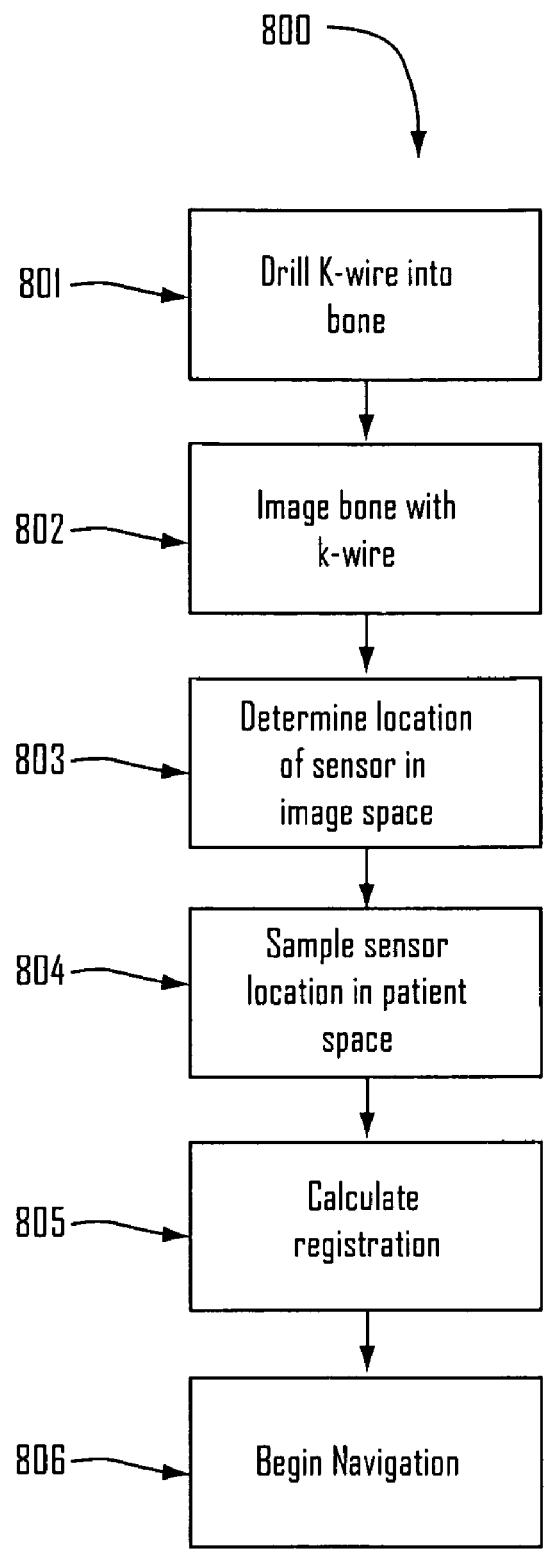
FIG. 8 depicts a method using a tracked K-wire according to an embodiment of the invention.

To facilitate registration, the tracked K-wire may be drilled into bone (e.g., the vertebral body) as indicated in FIG. 8. This can be done with or without image guidance or by using conventional image guidance such as X-ray. Once in place, markings on the K-wire or the shape of the K-wire are used in the manner described in U.S. Pat. No. 6,785,571 to enable the location of the position-indicating elements to be determined. The method may proceed as follows. See flow chart 800.

One or more K-wires may be drilled or attached into the bone (step 801). The K-wires are imaged (step 802). The imaging may be done using a scanner such as, for example, a computerized tomography (CT) scanner, a fluoroscope, biplane fluoroscope, or other device capable of determining the location of the position-indicating elements in the K-wires or indicator markings whose position and orientation is known relative to the position-indicating element. In one embodiment (described above), the markings may be on the K-wire in a known location relative to the position-indicating element. In one embodiment, the markings may be on the position-indicating element itself.

Next, the images are used to determine the location of the position-indicating element in image space (Step 803) (i.e., in the coordinate system intrinsic to the images). In some embodiments this can be performed automatically using a computerized segmentation process, in other embodiments this may be performed manually. The location of the position-indicating element in patient space (i.e., the coordinate system intrinsic to the position sensor) is then determined through sampling the position and orientation of the position indicating elements with the position sensor (Step 804). A registration process (step 805) may also be performed. Various registration techniques are known. In one embodiment, a singular valued decomposition is used. In another embodiment, an iterative closest points technique is used. Other techniques can be used.

Navigation (e.g., using a tracked tool) may then be commenced (Step 806). Navigation may include using a tracked tool (e.g., a tool that contains a position-indicating element) in the position sensor volume. The patient space coordinates may be converted (e.g., using the registration of step 805) to image space and the location and orientation of the tracked tool may be displayed on the images. In one embodiment, the tracked tool can be another K-wire. In another embodiment, the tracked tool can be a probe or any other device that contains one or more position-indicating elements.

Dynamic referencing may be used to compensate for bone (or other) movement. In practice, it can also be used to track an individual bone or bone fragment; the method of use of the invention for this purpose is essentially the same in these cases. To facilitate dynamic referencing one or more of the tracked K-wires is placed into the bone as detailed in FIG. 9 in flowchart 900.

Figure 9:
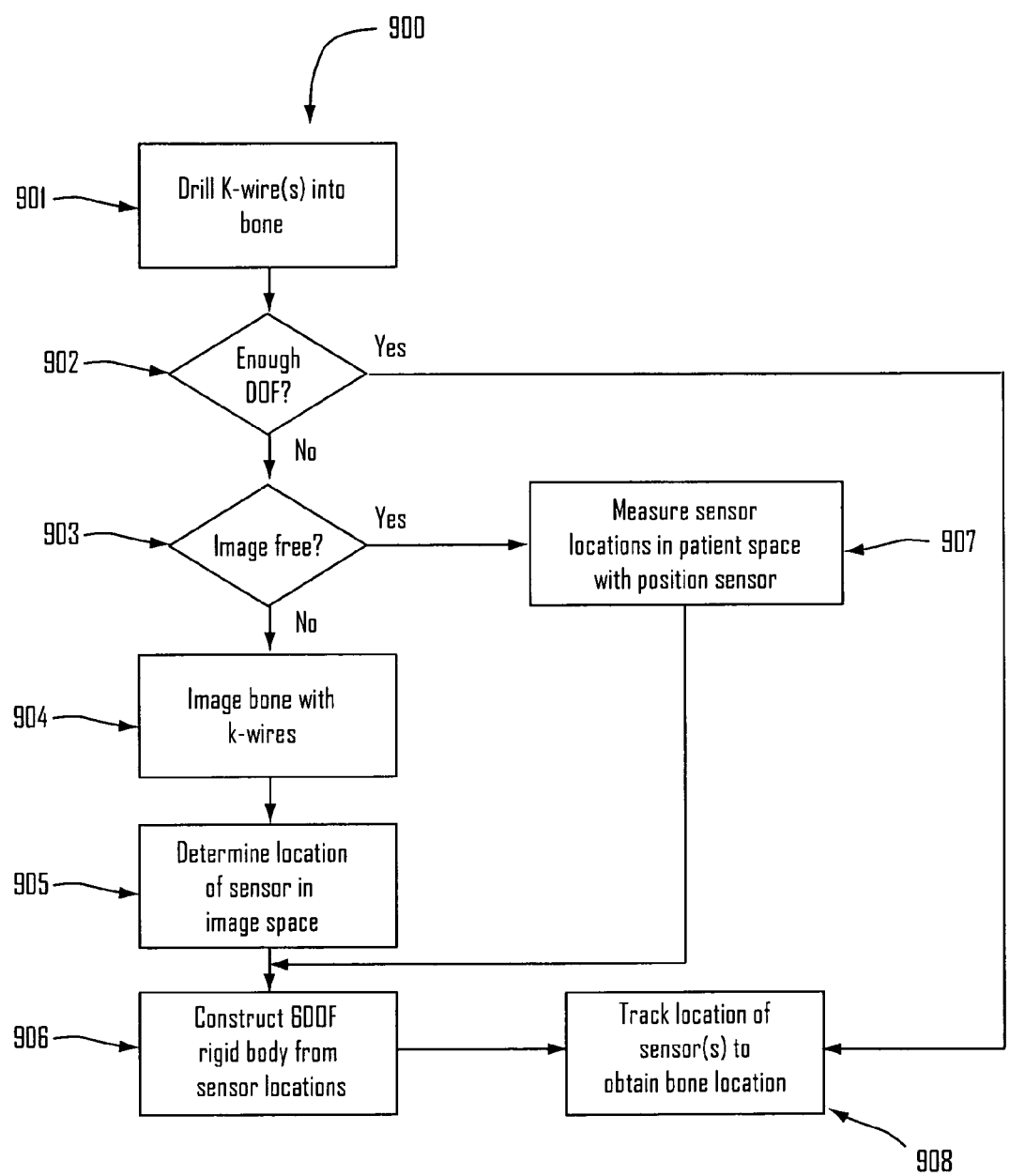
FIG. 9 depicts a method using a tracked K-wire according to an embodiment of the invention.

As shown in FIG. 9 one or more of the K-wires may be drilled into the bone or bone fragment. The number used depends on the number of degrees of freedom (DOF) that the position-indicating element and position sensor are capable of measuring, the number of position-indicating elements present in the K-wire, and the accuracy required. Normally the best accuracy is obtained by tracking the bone in 6 degrees of freedom, however, this may not be required for some applications (e.g., in which some components of motion are small). If 6 DOF position-indicating elements are used, only a single K-wire is required, as the position-indicating element embedded in the bone measures three translations and three rotations. If 5 DOF position-indicating elements are used, at least 2 K-wires are required to fully describe the motion in 6 DOF. If 3 DOF position-indicating elements are used, at least 3 are required to describe the motion in 6 DOF. In decision box 902, if enough DOF can be measured using a single K-wire, then it is then possible to directly track the motion of the bone (in the required number of DOF) to which it is attached as indicated in box 908. If instead, multiple K-wires are used, they are drilled into the object to be tracked. To determine extra DOF, at least two approaches can be used. In decision box 903, if an imaging method is to be used, the bone or fragment with K-wires is imaged as indicated in 904. Using methods described above (or otherwise), the locations and/or orientations of the position-indicating elements is determined in image space as indicated in box 905. Using the location and/or orientation information, methods are employed in box 906 to create a 6 DOF "rigid body" whose motion can be determined and tracked in box 908.

If in decision box 903 an image free method is to be used, the positions of the position-indicating elements are determined by directly measuring the locations of each of the position-indicating elements embedded in the bone using the K-wire as indicated in box 907. Using the location and/or orientation information, methods are employed in box 906 to create a 6 DOF "rigid body" whose motion can be determined and tracked in box 908.

Initial implantation of K-wires for use in dynamic referencing or for registration may be performed using a live imaging device such as, for example, fluoroscopy, ultrasound, or other imaging apparatus, or may be performed using an initial "temporary registration." In this scenario, a temporary registration may be performed using, for example, a paired point surface registration or a skin patch, as described in U.S. patent application Ser. No. 11/271,899, by Glossop, entitled "Integrated Skin-Mounted Multifunction Device for use in Image Guided Surgery," which is hereby incorporated by reference herein in its entirety. This temporary registration may then be used to roughly guide the K-wires that will be used for the high fidelity registration into place. Similarly, a "temporary dynamic referencing device" such as, a skin patch may be used to help implant the K-wires that may be used for the high fidelity dynamic referencing or fragment tracking.

Figure 10:
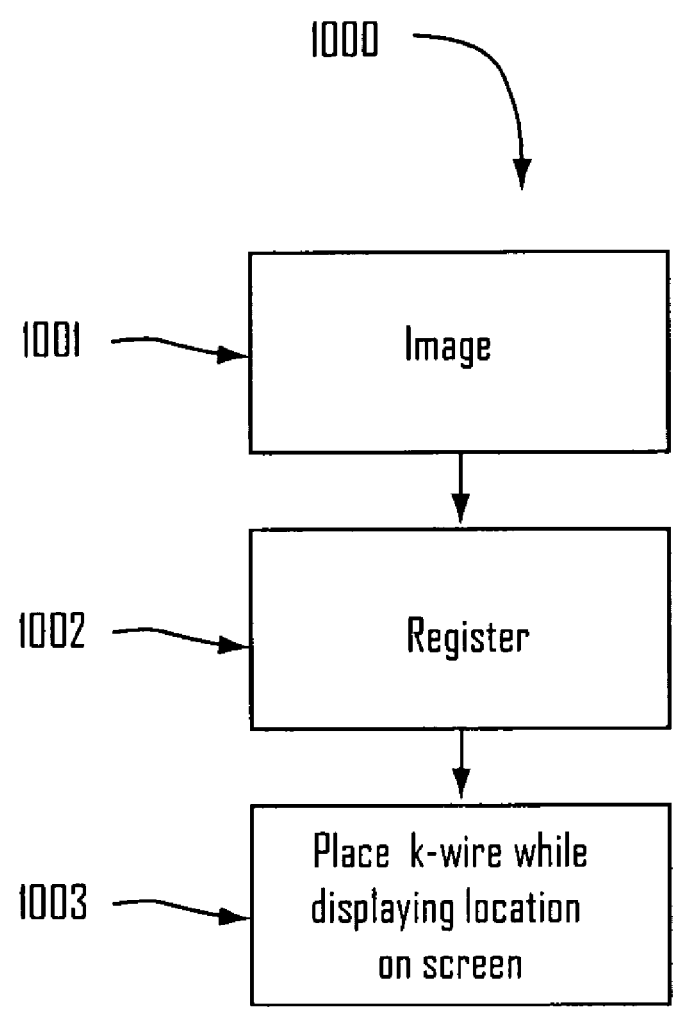
FIG. 10 depicts a method using a tracked K-wire according to an embodiment of the invention.

The tracked K-wire can be used as a guided instrument as indicated in FIG. 10, flowchart 1000. In an embodiment, the bone is first imaged (Step 1001). Next it is registered (Step 1002). This may be done using a number of different techniques known in the art, in addition to the embodiment described herein. The accuracy of the registration may then be verified using technologies known in the art. Examples of such verification materials and methods may be found in U.S. patent application Ser. No. 11/059,336 (published as U.S. Patent Publication No. 20050182319) by Glossop, which is incorporated by reference herein in its entirety. Finally, the tracked K-wire is inserted into the drill and while watching the progress of the drill on the images displayed on the computer system, it is drilled into the bone as shown in 1003. The registered image guided surgery system is used to position and orient the K-wire and monitor its location and orientation as it is drilled into the bone.

In one embodiment, the wire may be inserted into a cannulated drill onto which the slip coupling mechanism is attached. The wire may be seated so that the contact points of the K-wire electrically connect with the rotating part of the slip coupling and the hexagonal portion of the K-wire is engaged with the slip coupling. The chuck of drill is tightened. The connector cable of the coupling is connected to the position sensor. The drill and K-wire are brought into the volume and drilling is commenced. The position and orientation of the position-indicating element is displayed in real time as the drilling occurs. In some embodiments, the display may only be activated when drilling stops.

The device described can be configured in numerous variations, including a version where the contact rings on the K-wire are used as rotational contact members as mentioned previously. Different methods of ensuring movement of the encoder shaft may also be employed beside the hex head. These may include square heads, triangular heads, stepped heads etc. In some configurations, the K-wire contacts may act as partially rotating, relying on friction alone. In such cases part of the slip will occur at the K-wire contacts and part at the slip-coupling contacts.

Partial slippage at the K-wire contacts is permitted as it is not required that rotational coupling should be 1 K-wire rotation to 1 slip coupling rotation. Coupling can also take place at any location along the K-wire shaft. In cases where wireless position-indicating elements are employed, the slip coupling is obviously not required.

While various embodiments have been described on connection with a K-wire, the principles of the invention can be applied to other devices as well. For example, the invention can be applied to a screw, drill bit, pin, stylette, guidewire, and other shaft like devices or other devices. In forms that employ wireless position-indicating elements, the same form of the elongated member can be used but, the elongated member itself or conductive elements placed within and attached to the position-indicating element can act as an antenna to broadcast the signal from the wireless position-indicating element. Other embodiments and alternatives may be used.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

The invention claimed is:

1. A device for image guided surgery that includes a k-wire for insertion in an anatomical body, the k-wire comprising:
   at least one electromagnetic position-indicating element, located in a distal end of the elongated member and capable of providing the position and orientation of the location of the position-indicating element;
   at least one conductive lead-wire from which signals are carried from the at least one electromagnetic position-indicating element at the distal end along at least a portion of a length of the k-wire to a proximal end;
   a plurality of connection bands associated with the k-wire, wherein the plurality of connection bands are located at the proximal end and connect the at least one conductive lead-wire to an electromagnetic position sensor system.

2. The device of claim 1, wherein the connection bands are configured to facilitate axial rotation of the k-wire while maintaining contact with the electromagnetic position sensor system.

3. The device of claim 1, wherein the connection bands connect the at least one conductive lead wire to the electromagnetic position sensor system via a rotary slip coupling that permits rotational movement of the k-wire while maintaining electrical contact between the electromagnetic sensor system and the position indicating element.

4. The device of claim 1, wherein a tip of the k-wire includes a sharp point.

5. The device of claim 1, wherein at least part of the k-wire is threaded.

6. The device of claim 1, wherein the at least one position-indicating element contains radio-opaque markings.

7. The device of claim 6, wherein the radio-opaque markings further form a pattern that can be used to encode information relating to the k-wire.

8. The device of claim 7, wherein the information can be decoded using X-rays.

9. The device of claim 1, wherein the k-wire includes an integrated identification system encoding information relating to the elongated member.

10. The device of claim 9, wherein the identification information includes at least one of:
    a pattern of dark and light regions that effectively constitute barcode or other similar code and that can be optically determined;

a plurality of switches that can be used to construct a binary number that encodes information;
a memory device; or
an RFID device.

11. The device of claim 1, wherein the conductive elements are of the same or smaller diameter than the remainder of the k-wire.

12. The device of claim 1, wherein the k-wire includes recesses, and the plurality of connection bands are located in the recesses.

13. The device of claim 1, wherein the plurality of connection bands is located in recesses of the k-wire and is flush with the k-wire.

14. The device of claim 1, wherein the plurality of connection bands are substantially near each other and are separated by an insulating portion of the k-wire.

15. The device of claim 1, wherein the plurality of connection bands are rings located around the k-wire.

16. The device of claim 1, wherein the plurality of connection bands are rings located around the k-wire in recesses of the k-wire.

17. The device of claim 1, wherein the k-wire includes a groove along a length of the k-wire between the at least one electromagnetic position-indicating element and plurality of connection bands, and wherein the at least one conductive lead-wire is located in the groove.

18. The device of claim 17, wherein the k-wire includes a further groove at the distal end, and wherein the at least one electromagnetic position-indicating element is located in the further groove.

19. An apparatus for dynamically referencing a portion of an anatomy of a patient, the apparatus comprising an electromagnetic position sensor system and at least one instrumented K-wire, the at least one instrumented K-wire including at least one electromagnetic position-indicating element located in a distal end of an elongated member insertable in an anatomical body, the at least one electromagnetic position-indicating element being capable of providing position and orientation of a location of the position-indicating element, wherein the at least one instrumented K-wire further includes a plurality of connection bands located at a proximal end of the elongated member, and at least one conductive lead-wire for carrying signals from the at least one electromagnetic position-indicating element at the distal end along at least a portion of a length of the elongated member to the proximal end.

20. The apparatus of claim 19, further comprising a computer system, the computer system including a readable storage medium tangibly embodying a program of instructions executable by the apparatus to track a portion of the anatomical body to which the at least one instrumented K-wire is secured by tracking the position and orientation of the at least one position-indicating element.

21. The apparatus of claim 19, wherein the elongated member includes recesses, and the plurality of connection bands are located in the recesses.

* * * * *